United States Patent [19]
Wilk et al.

[11] Patent Number: 5,303,719
[45] Date of Patent: Apr. 19, 1994

[54] SURGICAL METHOD AND ASSOCIATED INSTRUMENT ASSEMBLY

[76] Inventors: Peter J. Wilk, 185 West End Ave., New York, N.Y. 10023; Jonathan Tiefenbrun, 62 Country Rd., Mamaroneck, N.Y. 10543

[21] Appl. No.: 83,064

[22] Filed: Jun. 25, 1993

Related U.S. Application Data

[63] Continuation-in-part of Ser. No. 930,159, Aug. 14, 1992.

[51] Int. Cl.⁵ ............................................. A61B 17/36
[52] U.S. Cl. ...................... 128/898; 606/16; 606/32; 606/159; 128/831
[58] Field of Search .............. 606/7, 15, 16, 159; 128/830, 831, 898

[56] References Cited

U.S. PATENT DOCUMENTS

| | | | |
|---|---|---|---|
| 3,858,586 | 1/1975 | Lessen | 128/831 |
| 4,119,098 | 10/1978 | Bolduc et al. | 128/831 |
| 4,185,618 | 1/1980 | Corey | 128/831 |
| 4,445,892 | 5/1984 | Hussein et al. | 606/15 X |
| 4,700,701 | 10/1987 | Montaldi | 128/831 X |
| 4,860,743 | 8/1989 | Abela | 606/16 X |
| 5,029,588 | 7/1991 | Yock et al. | 606/7 X |
| 5,032,123 | 7/1991 | Katz et al. | 606/15 |
| 5,041,121 | 8/1991 | Wondrazek et al. | 606/15 X |
| 5,095,917 | 3/1992 | Vancaillie | 128/831 |
| 5,129,895 | 7/1992 | Vassiliadis | 606/17 X |
| 5,147,353 | 9/1992 | Everett | 128/831 X |
| 5,163,935 | 11/1992 | Black et al. | 606/15 X |

*Primary Examiner*—Peter A. Aschenbrenner
*Attorney, Agent, or Firm*—R. Neil Sudol; Henry D. Coleman

[57] ABSTRACT

A surgical sterilization method utilizes an elongate operating instrument assembly having a distal end portion which is inserted into a patient's Fallopian tube. The instrument assembly is operated to destroy cells along an inner surface of the Fallopian tube essentially throughout a segment thereof, while maintaining an outer surface of the Fallopian tube intact. Upon operation of the instrument assembly to destroy cells along the inner surface of the Fallopian tube segment, the tube is collapsed along the treated segment, thereby adhering the inner surface of the Fallopian tube to itself to seal the tube.

27 Claims, 3 Drawing Sheets

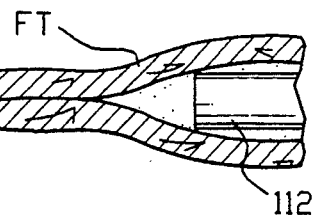
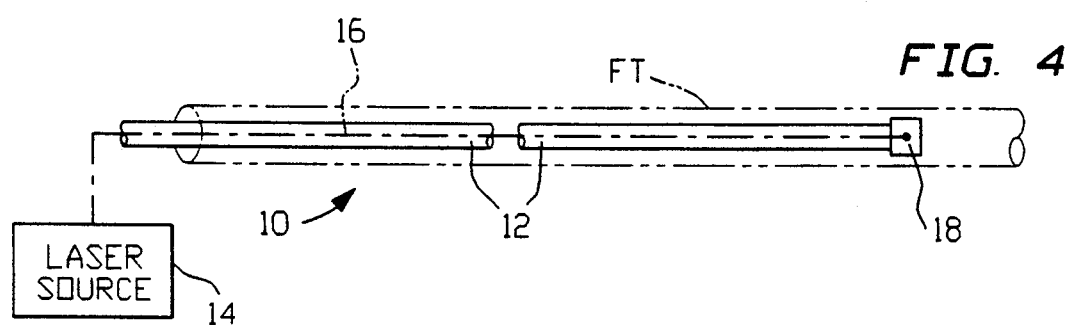
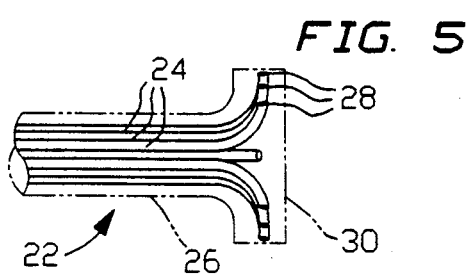
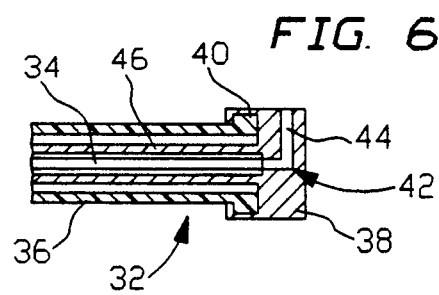
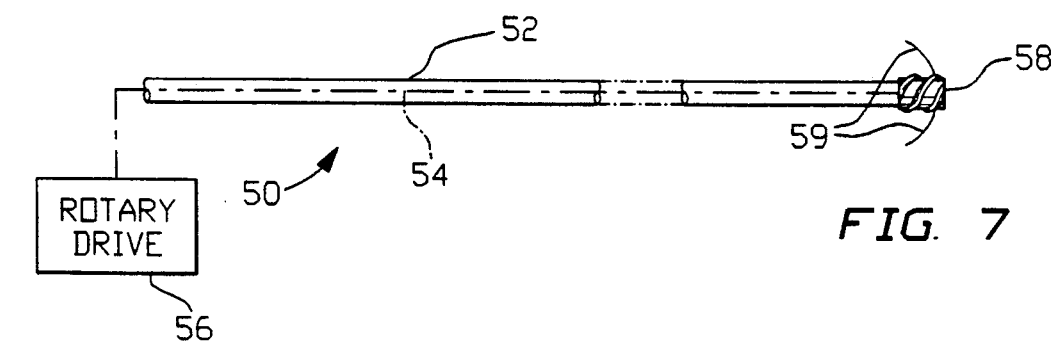
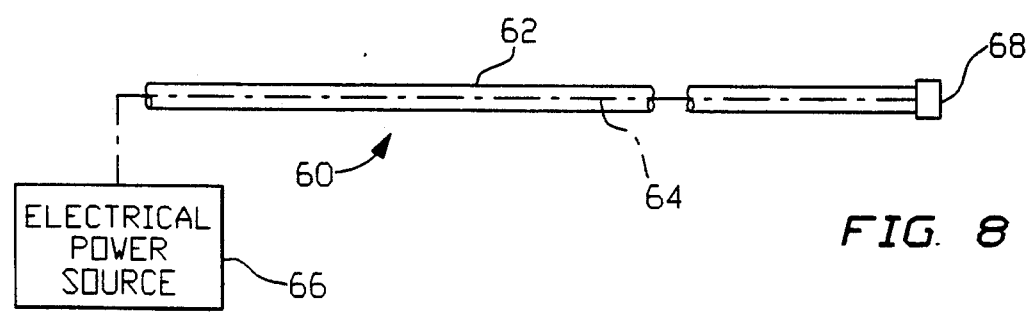

SURGICAL METHOD AND ASSOCIATED INSTRUMENT ASSEMBLY

CROSS-REFERENCE TO RELATED APPLICATION

This application is a continuation-in-part of application Ser. No. 930,159 filed Aug. 14, 1992.

BACKGROUND OF THE INVENTION

This invention relates to a method for sterilizing a woman. More particularly, this invention relates to a method for closing or sealing a Fallopian tube. This invention also relates to an associated device for use in the method.

A common method for female sterilization is a tubal ligation. Conventionally, this operation was performed in the operating room, as open surgery. Lately, it has become possible to tie or clip a Fallopian tube in a laparoscopic surgical procedure. Laparoscopy involves the piercing of the abdominal wall with a trocar and the insertion of a tubular port member called a "trocar sleeve" or "laparoscopic cannula" through the perforation. A laparoscopic instrument for applying a surgical clip to the Fallopian tube is inserted through the trocar sleeve.

Generally, upon the disposition of the first trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

The problem with laparoscopic surgery is that it must still be performed in the hospital. It cannot be performed in doctors' offices as flexible endoscopic procedures. Moreover, in comparison, for example, with gastrointestinal endoscopy, the patient still experiences substantial trauma, and the convalescence and hospitalization costs can be great.

OBJECTS OF THE INVENTION

An object of the present invention is to provide a surgical method for a new method for female sterilization.

Another object of the present invention is to provide such a method which is less traumatic to the patient than conventional open incision surgery and perhaps less traumatic than lapaoscopic surgery.

Another, more particular, object of the present invention is to provide such a method which is performed endoscopi ally via the patient's vagina, rather than laparoscopically through abdominal incisions.

A further object of the present invention is to provide an associated surgical device for performing the method of the invention.

These and other objects of the present invention will be apparent from the drawings and detailed descriptions herein.

SUMMARY OF THE INVENTION

A surgical method comprises' in accordance with the present invention, the steps of (a) providing an elongate operating instrument assembly having a distal end portion, (b) inserting the distal end portion of the instrument assembly into a patient's Fallopian tube, (c) operating the instrument assembly to destroy cells along an inner surface of the Fallopian tube essentially throughout a segment thereof, while maintaining an outer surface of the Fallopian tube intact, and (d) upon operation of the instrument assembly to destroy cells along the inner surface of the Fallopian tube, collapsing the tube along the treated segment, thereby adhering the inner surface to itself to seal the Fallopian tube.

According to another feature of the present invention, the operation of the instrument assembly entails the step of feeding a fluidic composition to a distal end of the instrument assembly and applying the fluidic composition to the inner surface. The fluidic composition may be a biological glue or a powdered substance such as talc and may be applied to the inner surface of the Fallopian tube by a spraying process. Alternatively, the fluidic composition may be brushed onto the inner surface of the Fallopian tube. In any case, the fluidic substance functions to destroy the cells of the Fallopian tube to enable adherence of the inner surface of the tube to itself upon implementation of the collapsing step.

Where the instrument assembly includes an optical fiber and a laser source connected to the fiber at a proximal end thereof, the operation of the instrument assembly includes the step of transmitting electromagnetic radiation along the fiber from the source to the inner surface at a distal end of the fiber. A head at the distal end of the fiber may be rotated to emit the electromagnetic radiation in an arc along the inner surface. Alternatively, the instrument assembly may include a plurality of optical fibers having different outlets disposed in a circular array at the distal end of the instrument assembly, electromagnetic radiation being transmitted from the source along the fibers and out through the outlets.

Where the instrument assembly includes an electrical lead and a source of electrical power connected to the lead at a proximal end thereof, the operation of the instrument assembly includes the steps of transmitting electrical power from the source to a contact at a distal end of the lead and placing the contact in electrically conductive engagement with the inner surface of the Fallopian tube.

Where the instrument assembly includes a drill bit at a distal end of the instrument assembly and means operatively connected to the drill bit for rotating the drill bit, the operation of he instrument assembly includes the step of actuating the means for rotating and placing the drill bit in contact with the inner surface of the Fallopian tube.

Where the instrument assembly includes an elongate mesh, the operation of the instrument assembly includes the step of disposing the mesh in the Fallopian tube in contact with the inner surface thereof. The mesh may be made of bioabsorbable material.

Where the instrument assembly includes an elongate balloon, the operation of the instrument assembly includes the steps of disposing the balloon in a collapsed configuration in the Fallopian tube and subsequently inflating the balloon so that the balloon is in contact with the inner surface of the Fallopian tube. The balloon may be made of bioabsorbable material and/or provided along an outer surface with a layer of biocompatible adhesive. In the latter case, the method further comprises the step of adhering the outer surface of the balloon to the inner surface of the Fallopian tube via the layer of biocompatible adhesive.

According to another feature of the present invention, the insertion of the instrument assembly includes the step of inserting the distal end portion of the instrument assembly through the patient's vagina, cervix and uterus into the Fallopian tube. In this case, the distal end portion of the instrument assembly is preferably flexible to enabling a bending of the distal end portion during the insertion thereof.

Where the instrument assembly includes an actuator at its proximal end, the actuator being operatively connected to the distal end portion of the instrument assembly, the bending of the distal end portion includes the step of operating the actuator to bend the distal end portion.

According to a further feature of the present invention, the step of collapsing the Fallopian tube includes the step of subjecting the Fallopian tube to a vacuum pressure. Where the instrument assembly includes a suction channel, air is sucked through the channel to collapse the Fallopian tube.

According to an additional feature of the present invention, the method further comprises the step of injecting a biocompatible adhesive into the Fallopian tube prior to the collapsing thereof, the adhesive facilitating adherence of the inner surface of the Fallopian tube to itself.

Where the instrument assembly includes an endoscope, the method also comprises the step of using the endoscope to visually monitor the Fallopian tube and destruction of inner surface cells thereof.

To implement the destruction of the inner layer of cells of the Fallopian tube, the inner surface may be subjected cauterization and/or an ultrasonic wave.

A Fallopian tube closure method in accordance with the present invention results in a seal of the Fallopian tube. A dye may be injected into the Fallopian tube, e.g., on a far side of the segment to test the integrity of the seal. If the dye penetrates through the sealing Fallopian tube, it can be observed with the endoscope. The dye can be X-ray opaque and detected via a fluoroscope or X-ray apparatus.

A surgical device for use in a sterilization operation comprises' in accordance with the present invention, (i) an elongate flexible endoscope having a biopsy channel and insertable through a patient's vagina, cervix and uterus into a Fallopian tube, (ii) an elongate operating instrument inserted through the biopsy channel of the endoscope, and (iii) an active surgical or operating component operatively connected to the instrument for destroying cells along an inner surface of the Fallopian tube essentially throughout a segment thereof, while maintaining an outer surface of the Fallopian tube intact.

The active component may include a conduit for feeding a fluidic composition to a distal end of the instrument and an applicator for applying the fluidic composition to the inner surface of the Fallopian tube. The fluidic composition may be a biological glue, a powdered substance, or a talc. The applicator may include a nozzle or other element for spraying the fluidic composition onto the inner surface of the Fallopian tube or a brush for spreading the fluidic composition onto the inner surface of the tube.

Alternatively, the active component may include an optical fiber extending along the instrument and a laser source connected to the fiber at a proximal end thereof. More specifically, the active component may include a rotatable head at the distal end of the fiber. The rotation of the head causes the electromagnetic radiation to be emitted in an arc along the inner surface of the Fallopian tube.

In another alternative embodiment, a plurality of optical fibers are provided having different outlets disposed in a circular array at the distal end of the instrument. In either case the electromagnetic radiation is of an intensity sufficient to destroy the cells of the inner surface of the Fallopian tube.

The Fallopian tube cells may alternatively be destroyed by electrical current conducted from an electrical lead extending along the instrument from a source of electrical power. A contact is operatively connected to the electrical lead at the distal end of the instrument for cauterizing the tissues of the Fallopian tube.

The target Fallopian tube tissues may be destroyed echanically by a drill bit disposed at a distal end of the instrument. A rotary drive is operatively connected to the drill bit for rotating the drill bit. The surgeon or operator manipulates the endoscope and the surgical instrument to ensure that a sufficient area of the Fallopian tube is destroyed.

According to another feature of the present invention, the active component includes an elongate mesh and means for disposing the mesh in the Fallopian tube in contact with the inner surface thereof. The mesh is preferably made of bioabsorbable material.

In another alternative embodiment, the active component includes an elongate balloon, means for disposing the balloon in a collapsed configuration in the Fallopian tube and means for inflating the balloon so that the balloon is in contact with the inner surface.

A method for closing a Fallopian tube in a sterilization procedure in accordance with the present invention results in less pain to the patient than the conventional techniques. In addition, the surgical procedure may be performed in the surgeon's office. General anesthesia is not required.

BRIEF DESCRIPTION OF THE DRAWING

FIG. 3 is partially a partial schematic side elevational of the endoscopic tissue destruction device of FIGS. 1 and 2 and partially a cross-sectional view of the Fallopian tube, on an enlarged scale, showing a subsequent step in a method in accordance with the present invention.

FIG. 4 is partially a schematic side elevational view and partially a block diagram of an endoscopic laser device for treating a Fallopian tube in a method in accordance with the present invention.

FIG. 5 is a partial side elevational view, on an enlarged scale, of another optical fiber bundle in an endoscopic laser device for treating a Fallopian tube in a method in accordance with the present invention.

FIG. 6 is a side elevational view, on an enlarged scale, of an optical fiber head in an endoscopic laser device for treating a Fallopian tube in a method in accordance with the present invention.

FIG. 7 is partially a schematic side elevational view and partially a block diagram of an endoscopic surgical drill device for treating a Fallopian tube in a method in accordance with the present invention.

FIG. 8 is partially a schematic side elevational view and partially a block diagram of an endoscopic surgical cauterization device for treating a Fallopian tube in a method in accordance with the present invention.

DETAILED DESCRIPTION

Figure 1:
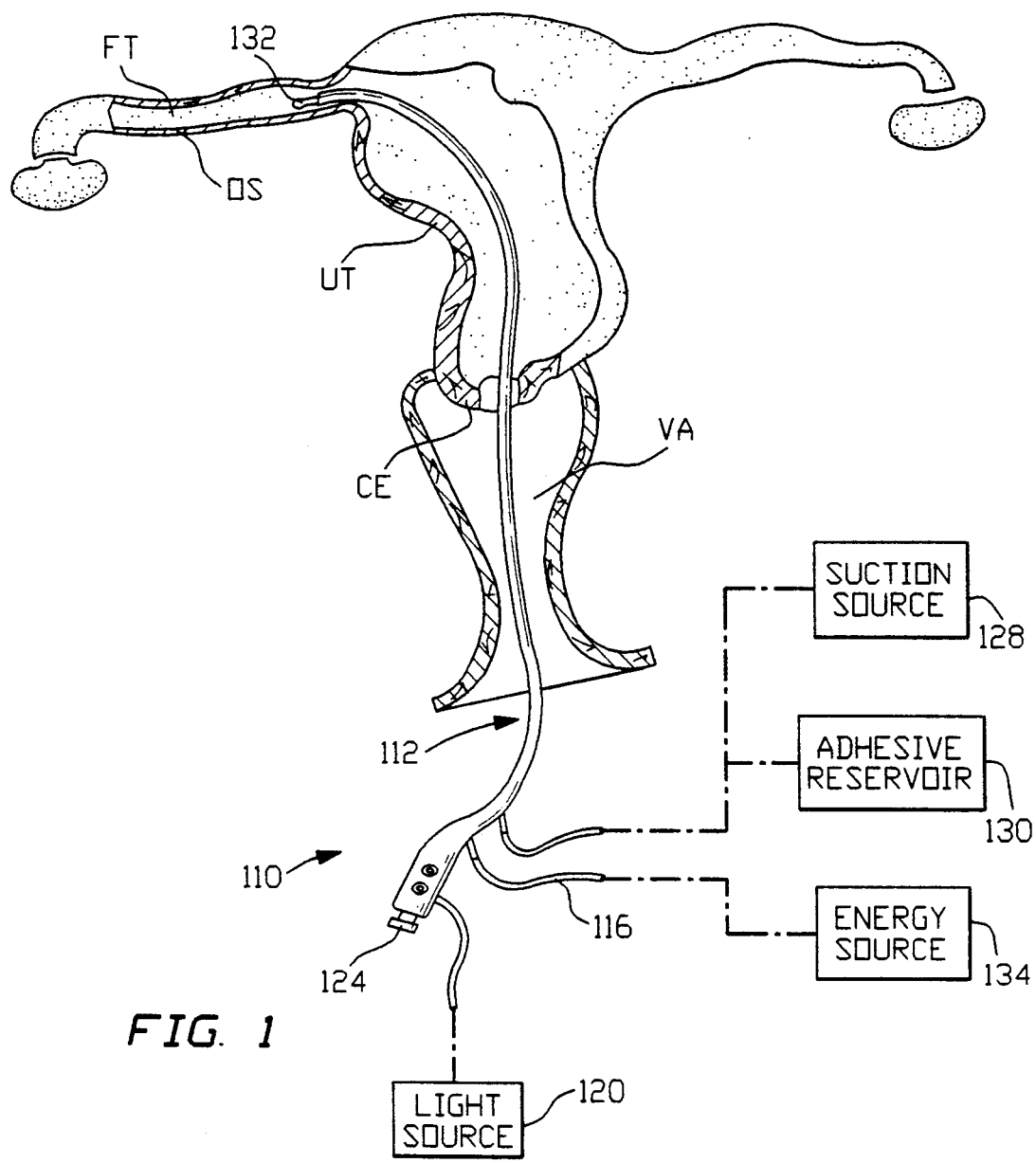
FIG. 1 is a schematic elevational view, partially broken away, of female reproductive apparatus' showing an endoscopic tissue destruction device inserted through the vagina, cervix and uterus into a Fallopian tube in a procedure in accordance with the present invention.
Figure 2:
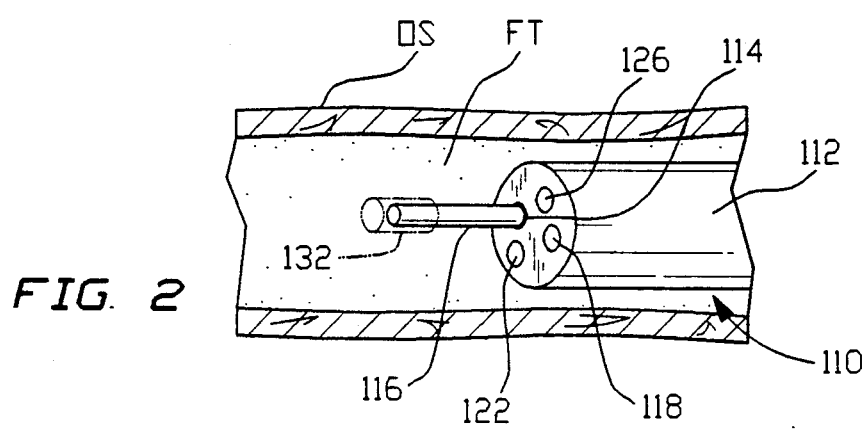
FIG. 2 is partially a schematic perspective of a distal end of the endoscopic tissue destruction device of FIG. 1 and partially a cross-sectional view of a Fallopian tube, on an enlarged scale, showing a step in a method in accordance with the present invention.

As illustrated in FIGS. 1 and 2, a surgical device or instrument assembly 110 for use in a sterilization operation comprises an elongate flexible endoscope 112 having a biopsy channel 114 (FIG. 2) through which an elongate flexible endoscopic surgical instrument 116 is inserted. In a female sterilization procedure, endoscope 112 is inserted through the patient's vagina VA, cervix CE and uterus UT into a Fallopian tube FT.

Endoscope 112 includes a fiber optic illumination guide 118 (FIG. 2) operatively connected to a light source 120 (FIG. 1), a fiber optic image guide 122 (FIG. 2) operatively connected to an eyepiece 124 (FIG. 1) or video monitor (not shown), and an ancillary longitudinally extending channel or conduit 126 (FIG. 2) connectable to a suction source or vacuum generator 128 or a pressurizable adhesive reservoir 130 (FIG. 1).

Surgical instrument 116 is provided at a distal end with an active surgical or operating component 132 for destroying cells along an inner surface of Fallopian tube FT essentially throughout a segment thereof, while maintaining an outer surface OS of the Fallopian tube intact. Surgical instrument 116 and/or endoscope 112 is manipulated from outside the patient to move operating component 132 sufficiently close to the inner wall of Fallopian tube FT to enable adequate tissue destruction by operating component 132.

Operating component 132 is operatively connected at a proximal end of surgical instrument 116 to an energy source 134 which provides the operating component 132 with the energy for organic tissue mutilation. As will be clear from FIGS. 4–12 and the accompanying description, the energy generated by source 134 may be electromagnetic (laser radiation), mechanical (rotary), electrical, pressurized fluidic substance (adhesive, talc), etc. Alternatively, as discussed hereinafter with reference to FIGS. 9 and 12, operating component 132 may take the form of a net or balloon engageable with the inner surface of Fallopian tube FT.

Upon the destruction of a layer of cells along an inner surface segment of Fallopian tube FT, suction source 128 is connected to channel 126 for subjecting Fallopian tube FT to a vacuum, thereby collapsing Fallopian tube FT inwardly upon itself (FIG. 3) and inducing the mutilated inner surface of the Fallopian tube FT to adhere to itself in a seal or closure. The sealing of Fallopian tube FT upon the vacuum induced collapse thereof may be facilitated through the injection of biocompatible adhesive from reservoir 130, in those cases where cell destruction is accomplished by a means other than adhesive application.

As illustrated in FIG. 4, surgical instrument 16 may take the form of a device 10 comprising an elongate tubular operating instrument 12 insertable through biopsy channel 114 (FIG. 2) for use in closing a Fallopian tube FT. An active component in the form of a laser source 14 is operatively connected to instrument 12 for generating a laser beam to destroy cells along an inner surface of Fallopian tube FT essentially throughout a segment thereof. Laser source 14 has an optical output fiber 16 extending the length of instrument 12.

During a surgical procedure utilizing device 10 of FIG. 4 in conjunction with endoscope 12 of FIGS. 1 and 2, instrument 12 is pushed through biopsy channel 114 until an operative tip or head 18 at the distal end of instrument 12 is ejected from the biopsy channel 114 into Fallopian tube FT. Operative tip or head 18 constitutes a specific implementation of operating component 32 (FIGS. 1 and 2). Source 14 is operated to emit a beam of coherent monochromatic electromagnetic radiation through fiber 16 and head 18 as instrument 12 is pulled in a proximal direction through biopsy channel 114.

The laser beam emitted by source 14 and transmitted along fiber 16 has such a power as to partially destroy a layer of tissue along an inner surface of Fallopian tube FT. The energy of the beam is not so great as to penetrate or pierce the tube. Accordingly, an outer surface of Fallopian tube FT is maintained intact. The speed at which instrument 12 is pulled through Fallopian tube FT is low enough to ensure a sufficient mutilation of the inner surface of the Fallopian tube FT by the laser beam.

As illustrated in FIG. 5, another laser instrument 22 for use in treating a Fallopian tube FT pursuant to the procedure described hereinabove with reference to FIGS. 1-3 comprises a plurality of optical fibers 24 extending longitudinally through a sheath 26. At a distal end of sheath 26, fibers 24 turn radially outwardly to provide a plurality of laser outlets 28 circumferentially spaced from each other about a head 30 at the distal end of sheath 26. Instrument 22 is used as described above with reference to FIG. 4. Sheath 26 may be twisted or rotated during an extraction stroke of the instrument to rotate head 30 and thereby emit in arcs a plurality of laser beams from outlets 28.

As shown in FIG. 6, another laser instrument 32 for use in treating Fallopian tube FT during a sterilization procedure as described hereinabove comprises a single optical fiber 34 extending longitudinally through tubular member 36. A head 38 is rotatably connected to tubular member 36 via an annular rib and groove assembly 40 at a distal end of tubular member 36. Head 38 carries an optical fiber segment 42 which is aligned at an input end with a distal end of fiber 34. An outlet portion 44 of fiber segment 42 is directed in a radial direction. Head 38 is connected to a rotary drive tube 46 coaxial with and disposed inside tubular member 36. During a proximally directed stroke of instrument 32, drive tube 46 is rotated to turn head 38, thereby emitting a laser beam from outlet portion 44 in a spiraling arc about the inner surface of Fallopian tube FT into which instrument 32 has been inserted.

It is to be noted that laser instruments 10, 22 and 32, which are alternative specific realizations of surgical instrument 16, may be inserted through a collapsible biopsy channel (not shown) provided in an endoscope sheath (not shown) removably attached to endoscope 12. Such a sheath is disclosed in U.S. Pat. No. 5,217,001, the disclosure of which is hereby incorporated by reference. Other equivalent methods for inserting surgical instrument 16 in tandem with endoscope 12 are within the contemplation of the present invention.

As illustrated in FIG. 7, another endoscopic instrument 50 for treating Fallopian tube FT in accordance with the method described hereinabove with reference to FIGS. 1-3 comprises a tubular member 52 traversed longitudinally by a rod or wire 54. Rod 54 extends from a rotary drive 56 to a drill head 58 rotatably mounted to the distal end of tubular member 52. After an insertion of tubular member 52 into Fallopian tube FT, e.g., via biopsy channel 114 of endoscope 12, the tubular member is pulled in the proximal direction while drive 56 and rod 54 rotate head 58, thereby at least partially destroying an inner layer of cells along the length of the Fallopian tube FT. The mutilation of the endothelial layer of the Fallopian tube FT results in adherence of the Fallopian tube to itself to close and seal the tube upon vacuum mediated collapse thereof. Drill head 58 may be provided with one or more whips 59 which pivot or bend radially outwardly during rotation of head 58. Whips 59 cut the inner Fallopian tube tissues and thereby destroy those tissues.

FIG. 8 depicts another endoscopic instrument 60 for at least partially destroying an endothelial layer of Fallopian tube FT, whereby the Fallopian tube adheres upon collapse thereof. Instrument 60 includes a tubular member 62 and an electrical lead 64 extending longitudinally through tubular member 62 from a source of electrical power or voltage 66 at a proximal end of tubular member 62. A cauterization contact 68 is operatively connected to lead 64 at the distal end of instrument 60. During a pulling of tubular member 62 in a proximal directed through Fallopian tube FT, electrical source 66 is operatively linked to contact 68 for transmitting a cauterizing current to the inner surface of the Fallopian tube, thereby destroying cells in the endothelial layer. It is to be noted that in a method using instrument 60 or any of the instruments described herein that it is necessary only to mutilate or destroy the endothelial layer to an extent sufficient to enable adherence of that layer to itself.

Figure 9:
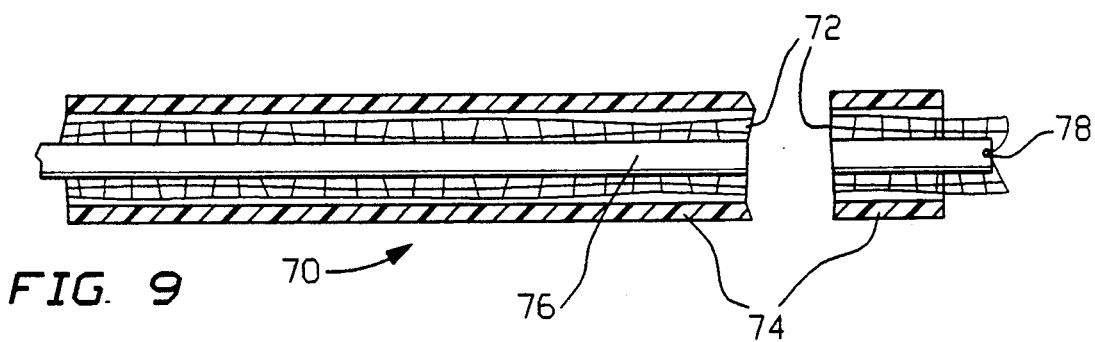
FIG. 9 is a partial cross-sectional view, on an enlarged scale, of a mesh delivery device for treating a Fallopian tube in a method in accordance with the present invention.

Adequate destruction of the endothelial layer of Fallopian tube FT can be alternatively achieved by inserting a foreign body into the Fallopian tube FT. As illustrated in FIG. 9, an endoscopic instrument 70 for inserting a foreign body in the form of a net or mesh 72 includes an elongate inserter tube 74 itself insertable through biopsy channel 114 of endoscope 12. Mesh 72 may have an inherent spring bias tending to open the mesh from a collapsed configuration to an opened configuration. Upon removal of tube 74 from about mesh 72 inside Fallopian tube FT, the mesh expands to contact the inner surface or endothelial layer of the Fallopian tube FT.

As further illustrated in FIG. 9, a rod 76 extends through tube 74 and is removably connected to mesh 72 at a distal end 78 of both the rod and the mesh. Rod 76 serves to hold the distal end of the mesh in a predetermined location inside the Fallopian tube FT while tube 74 is being withdrawn in a proximal direction. Upon withdrawal of a sufficient length of tube 74, rod 76 is pulled in the proximal direction through Fallopian tube FT. At that juncture, the expansion of the distal end portion of mesh 72 secures the mesh in Fallopian tube FT so that the mesh is not withdrawn along with the rod. It is to be noted that mesh 72 may be made of bioabsorbable material.

Figure 10:
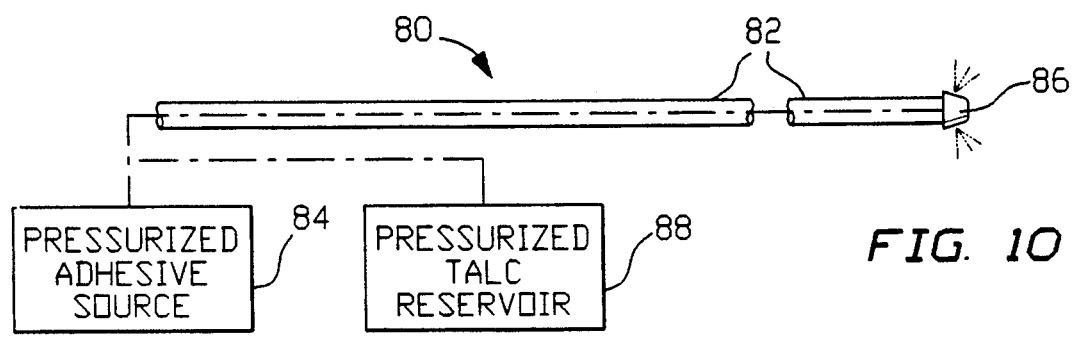
FIG. 10 is partially a schematic side elevational view and partially a block diagram of a glue or talc dispensing device for treating a Fallopian tube in a method in accordance with the present invention.

The foreign material deposited into Fallopian tube FT along the length thereof may alternatively take the form of a biological adhesive or a powdered substance such as talc. As illustrated in FIG. 10, an endoscopic instrument 80 for depositing or applying a glue to the inner surface of a Fallopian tube FT includes a tubular member 82 insertable through biopsy channel 114 of endoscope 12 and connected at a proximal end to a pressurized adhesive source 84. At a distal end, tubular member 82 is provided with a nozzle or spray head 86, which directs a spray of adhesive to the endothelial layer of Fallopian tube FT during an extraction stroke of tubular member 82.

Alternatively or additionally, tubular member 82 may be connected at the proximal end to a reservoir of talc 88 which is pressurized, for example, with a saline solution. During a spraying of the talc upon extraction of tubular member 82 from a Fallopian tube FT, the talc adheres to the inner surface of the Fallopian tube FT, thereby causing an inflammatory response which eventually destroys the anti-adherence character of the endothelial layer.

More generally, the instrument 80 of FIG. 10 is configured to feed a fluidic composition to the distal end of tubular member 82. Nozzle 86 serves to apply the fluidic composition to the inner surface of the Fallopian tube FT particularly during an extraction stroke thereof.

It is to be noted that some talc or adhesive may be dispensed during an insertion stroke of tubular member 82. However, it is preferable to dispense the fluidic foreign substance into the Fallopian tube FT during an extraction stroke of tubular member 82.

Figure 11:
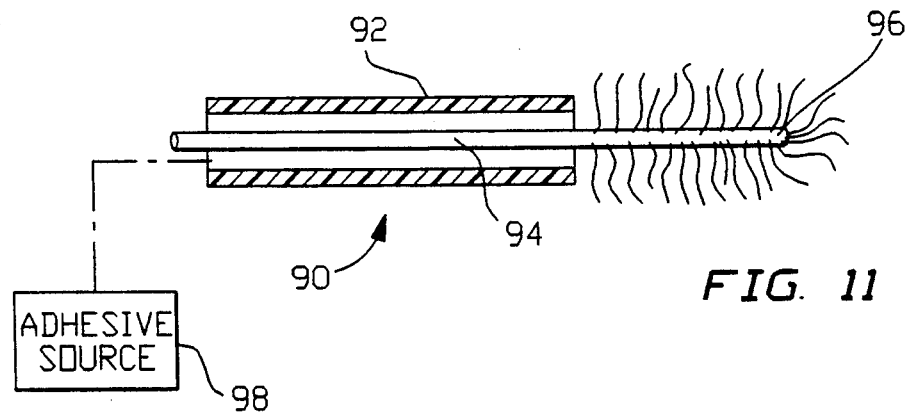
FIG. 11 is partially a schematic side elevational view and partially a block diagram of a glue dispensing device for treating a Fallopian tube in a method in accordance with the present invention.

As shown in FIG. 11, yet another endoscopic instrument 90 for dispensing or delivering a fluidic composition such as a biological adhesive or a fluidized talcum stream to Fallopian tube FT and for applying the fluidic composition to the endothelial layer of the Fallopian tube FT comprises a tubular member 92 in which a rod 94 is slidably inserted. At a distal end, rod 94 is provided with a brush head 96 for applying, to the inner surface of Fallopian tube FT during a withdrawal stroke of tubular member 92, fluidic material delivered to a proximal end of tubular member 92 from a pressurized source 98.

Figure 12:
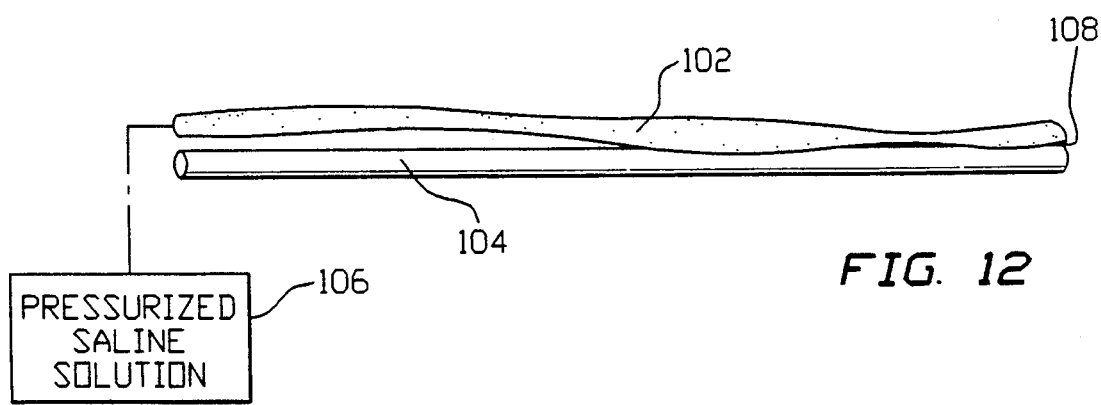
FIG. 12 is a device for placing a balloon inside a vein in a method in accordance with the present invention.

As illustrated in FIG. 12, another type of foreign body or substance insertable into Fallopian tube FT pursuant to the procedure described hereinabove with reference to FIGS. 1-3 takes the form of an elongate balloon 102. Balloon 102 is a form of operating component 32 and is removably attached to the distal end 108 of an inserter rod 104. At a proximal end, balloon 102 is connected to a source 106 of pressurized saline solution. Rod 104 is inserted from endoscope 12 into Fallopian tube FT together with balloon 102 in a deflated or collapsed configuration. Upon the attainment of a predetermined position inside the Fallopian tube FT by the distal end of rod 104 and balloon 102, saline solution is pumped from source 106 into balloon 102, thereby a least partially inflating the balloon. Rod 104 is then removed and balloon 102 further inflated by saline from source 106. Balloon 102 is preferably made of a bioabsorbable material. Balloon 102 may be provided along an outer surface with a layer of biologically compatible adhesive which adheres to the inner surface of Fallopian tube FT. Upon that adherence, the balloon may be actively depressurizing to pull the Fallopian tube FT inwardly upon itself.

Upon completion of an operation as described hereinabove with reference to FIGS. 1-3, a dye may be injected into the Fallopian tube, e.g., on a far side of the sealed segment to test the integrity of the seal. If the dye penetrates through the sealing Fallopian tube, it can be observed with the endoscope. The dye can be X-ray opaque and detected via a fluoroscope or X-ray apparatus.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising the steps of:
   providing an elongate operating instrument assembly having a distal end portion;
   inserting said distal end portion of said instrument assembly into a patient's Fallopian tube;
   operating said instrument assembly to destroy cells along an inner surface of said Fallopian tube essentially throughout a segment thereof, while maintaining an outer surface of said Fallopian tube intact; and
   upon operation of said instrument assembly to destroy cells along said inner surface, collapsing said Fallopian tube along said segment, thereby adhering said inner surface to itself to seal said Fallopian tube.

2. The method defined in claim 1 wherein said step of operating includes the step of feeding a fluidic composition to a distal end of said instrument assembly and applying said fluidic composition to said inner surface.

3. The method defined in claim 2 wherein said fluidic composition is a biological glue.

4. The method defined in claim 2 wherein said fluidic composition is a powdered substance.

5. The method defined in claim 4 wherein said fluidic composition is talc.

6. The method defined in claim 2 wherein said step of applying includes the step of spraying said fluidic composition onto said inner surface.

7. The method defined in claim 2 wherein said step of applying includes the step of brushing said fluidic composition onto said inner surface.

8. The method defined in claim 1 herein said instrument assembly includes an optical fiber and a laser source connected to said fiber at a proximal end thereof, said step of operating including the step of transmitting electromagnetic radiation along said fiber from said source to said inner surface at a distal end of said fiber.

9. The method defined in claim 8 wherein said step of operating further includes the step of rotating a head at said distal end of said fiber, thereby emitting said electromagnetic radiation in an arc along said inner surface.

10. The method defined in claim 8 herein said instrument assembly further includes a plurality of optical fibers having different outlets disposed in a circular array at said distal end of said instrument assembly, said step of operating including the step of transmitting electromagnetic radiation from said source along said fibers and out through said outlets.

11. The method defined in claim 1 herein said instrument assembly includes an electrical lead and a source of electrical power connected to said lead at a proximal end thereof, said step of operating including the steps of transmitting electrical power from said source to a contact at a distal end of said lead and placing said contact in electrically conductive engagement with said inner surface.

12. The method defined in claim 1 wherein said instrument assembly includes a drill bit at a distal end of said instrument assembly and means operatively connected to said drill bit for rotating said drill bit, said step of operating including the step of actuating said means for rotating and placing said drill bit in contact with said inner surface.

13. The method defined in claim 1 wherein said instrument assembly includes an elongate mesh, said step of operating including the step of disposing said mesh in said Fallopian tube in contact with said inner surface.

14. The method defined in claim 13 wherein said mesh is made of bioabsorbable material.

15. The method defined in claim 1 ,herein said instrument assembly includes an elongate balloon, said step of operating including the steps of disposing said balloon in a collapsed configuration in said Fallopian tube and subsequently inflating said balloon so that said balloon is in contact with said inner surface.

16. The method defined in claim 15 wherein said balloon is made of bioabsorbable material.

17. The method defined in claim 15 wherein said balloon is provided along an outer surface with a layer of biocompatible adhesive, further comprising the step of adhering said outer surface to said inner surface via said layer of biocompatible adhesive, said step of collapsing including the step of deflating said balloon to draw said inner surface in upon itself.

18. The method defined in claim 1 wherein said step of inserting includes the step of inserting said distal end portion of said instrument assembly through the patient's vagina, cervix and uterus into said Fallopian tube.

19. The method defined in claim 1 wherein said distal end portion is flexible, further comprising the step of bending said distal end portion during said step of inserting.

20. The method defined in claim 19 wherein said instrument assembly includes actuator means at a proximal end, said actuator means being operatively connected to said distal end portion, said step of bending including the step of operating said actuator means to bend said distal end portion.

21. The method defined in claim 1 wherein said step of collapsing includes the step of subjecting said Fallopian tube to a vacuum pressure.

22. The method defined in claim 21 wherein said instrument assembly includes a suction channel, said step of subjecting including the step of sucking air through said channel.

23. The method defined in claim 1, further comprising the step of injecting a biocompatible adhesive into said Fallopian tube prior to said step of collapsing, said adhesive facilitating adherence of said inner surface to itself.

24. The method defined in claim 1 wherein said instrument assembly includes an endoscope, further comprising the step of using said endoscope to visually monitor said Fallopian tube and destruction of inner surface cells thereof during said step of operating.

25. The method defined in claim 1 wherein said step of operating includes the step of cauterizing said inner surface.

26. The method defined in claim 1 wherein said step of operating includes the step of generating an ultrasonic wave and transmitting said ultrasonic wave to said inner surface.

27. The method defined in claim 1 wherein said steps of operating and collapsing result in a seal of said Fallopian tube, further comprising the step of injecting a dye into said Fallopian tube on a far side of said segment to test the integrity of said seal.

* * * * *

UNITED STATES PATENT AND TRADEMARK OFFICE
CERTIFICATE OF CORRECTION

PATENT NO. : 5,303,719
DATED : April 19, 1994
INVENTOR(S) : Peter J. Wilk and Jonathan Tiefenbrun It is certified that error appears in the above-indentified patent and that said Letters Patent is hereby corrected as shown below:

Column 1, line 67, change "endoscopi ally" to --endoscopically--.

Column 2, line 60, change "of he" to --of the--.

Column 3, line 45, insert --to-- after "subjected".

Column 4, line 30, change "echanically" to --mechanically--.

Column 6, line 21, change "16" to --116--; line 32, change "12" to --112--; line 38, change "32" to --132--.

Column 7, line 20, change "12" to --112--;

Column 8, line 2, change "12" to --112--; line 29, change "12" to --112--.

UNITED STATES PATENT AND TRADEMARK OFFICE
CERTIFICATE OF CORRECTION

PATENT NO. : 5,303,719
DATED : April 19, 1994
INVENTOR(S) : Peter J. Wilk and Jonathan Tiefenbrun It is certified that error appears in the above-indentified patent and that said Letters Patent is hereby corrected as shown below:

Column 9, line 4, change "32" to --132--; line 7, change "12" to --112--.

Column 10, line 4 (claim 8), change "herein" to --wherein--; line 14 (claim 10), change "herein" to --wherein--; line 21 (claim 11), change "herein" to --wherein--; line 42 (claim 15), change ",herein" to --wherein--.

Signed and Sealed this

Third Day of January, 1995

Attest:

BRUCE LEHMAN

Attesting Officer

Commissioner of Patents and Trademarks